(12) United States Patent
Wang et al.

(10) Patent No.: US 11,361,059 B2
(45) Date of Patent: **\*Jun. 14, 2022**

(54) FINGERPRINT ENHANCED AUTHENTICATION FOR MEDICAL DEVICES IN WIRELESS NETWORKS

(71) Applicant: MEDTRONIC MINIMED, INC., Northridge, CA (US)

(72) Inventors: Yongbo Wang, San Marino, CA (US); Bozhil Makaveev, Woodland Hills, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 31 days.

This patent is subject to a terminal disclaimer.

(21) Appl. No.: 16/940,337

(22) Filed: Jul. 27, 2020

(65) Prior Publication Data

US 2020/0356649 A1    Nov. 12, 2020

Related U.S. Application Data

(60) Continuation of application No. 15/686,553, filed on Aug. 25, 2017, now Pat. No. 10,776,466, which is a (Continued)

(51) Int. Cl.
*G06F 21/32* (2013.01)
*A61M 5/142* (2006.01)
(Continued)

(52) U.S. Cl.
CPC ......... *G06F 21/32* (2013.01); *A61M 5/14244* (2013.01); *G16H 20/17* (2018.01);
(Continued)

(58) Field of Classification Search
None
See application file for complete search history.

(56) References Cited

U.S. PATENT DOCUMENTS

| 4,755,173 A | 7/1988 | Konopka et al. |
| 5,391,250 A | 2/1995 | Cheney, II et al. |

(Continued)

FOREIGN PATENT DOCUMENTS

WO    WO-2013109737 A1 * 7/2013 ........... H04L 9/3271

OTHER PUBLICATIONS

Paul, Nathanael et al. "A review of the security of insulin pump infusion systems." Journal of diabetes science and technology vol. 5,6 1557-62. Nov. 1, 2011, doi:10.1177/193229681100500632 (Year: 2011).*

*Primary Examiner* — Devin C Hein

(74) *Attorney, Agent, or Firm* — Carter, DeLuca & Farrell LLP

(57) ABSTRACT

An infusion system to administer fluid is disclosed. The infusion system includes an infusion pump having a pump processor, a pump memory and a pump radio to enable bi-directional communication. The pump memory stores a plurality of fingerprint tokens and security conditions. The infusion system includes a controller with a processor, a controller memory and a controller radio to transmit and receive communication from the pump radio. The controller includes a fingerprint scanner and a graphical user interface (GUI) and controls to manipulate the GUI. The GUI and fingerprint scanner enable the controller to scan and determine tokens based on scanned fingerprints. Additionally, communication between the infusion pump and the controller establish relative proximity between the infusion pump and the controller such that when the relative proximity exceeds a threshold distance at least one of the plurality of security conditions is automatically matched.

20 Claims, 6 Drawing Sheets

Related U.S. Application Data division of application No. 14/132,347, filed on Dec. 18, 2013, now Pat. No. 9,779,226.

(51) Int. Cl.

| | | |
|---|---|---|
| *H04W 12/06* | (2021.01) | |
| *G16H 20/17* | (2018.01) | |
| *G16H 40/67* | (2018.01) | |
| *H04W 12/64* | (2021.01) | |
| *H04L 9/40* | (2022.01) | |

(52) U.S. Cl.
CPC .......... *G16H 40/67* (2018.01); *H04W 12/06* (2013.01); *H04W 12/64* (2021.01); *A61M 2205/276* (2013.01); *A61M 2205/3569* (2013.01); *A61M 2205/3592* (2013.01); *A61M 2205/502* (2013.01); *A61M 2205/505* (2013.01); *A61M 2205/507* (2013.01); *A61M 2205/52* (2013.01); *A61M 2205/609* (2013.01); *H04L 63/0861* (2013.01)

(56) References Cited

U.S. PATENT DOCUMENTS

| | | | |
|---|---|---|---|
| 5,485,408 | A | 1/1996 | Blomquist |
| 5,522,803 | A | 6/1996 | Teissen-Simony |
| 5,665,065 | A | 9/1997 | Colman et al. |
| 5,800,420 | A | 9/1998 | Gross et al. |
| 5,807,375 | A | 9/1998 | Gross et al. |
| 5,925,021 | A | 7/1999 | Castellano et al. |
| 5,954,643 | A | 9/1999 | Van Antwerp et al. |
| 6,017,328 | A | 1/2000 | Fischell et al. |
| 6,186,982 | B1 | 2/2001 | Gross et al. |
| 6,246,992 | B1 | 6/2001 | Brown |
| 6,248,067 | B1 | 6/2001 | Causey, III et al. |
| 6,248,093 | B1 | 6/2001 | Moberg |
| 6,355,021 | B1 | 3/2002 | Nielsen et al. |
| 6,379,301 | B1 | 4/2002 | Worthington et al. |
| 6,544,212 | B2 | 4/2003 | Galley et al. |
| 6,558,351 | B1 | 5/2003 | Steil et al. |
| 6,591,876 | B2 | 7/2003 | Safabash |
| 6,641,533 | B2 | 11/2003 | Causey, III et al. |
| 6,736,797 | B1 | 5/2004 | Larsen et al. |
| 6,749,587 | B2 | 6/2004 | Flaherty |
| 6,766,183 | B2 | 7/2004 | Walsh et al. |
| 6,801,420 | B2 | 10/2004 | Talbot et al. |
| 6,804,544 | B2 | 10/2004 | Van Antwerp et al. |
| 7,003,336 | B2 | 2/2006 | Holker et al. |
| 7,029,444 | B2 | 4/2006 | Shin et al. |
| 7,066,909 | B1 | 6/2006 | Peter et al. |
| 7,137,964 | B2 | 11/2006 | Flaherty |
| 7,303,549 | B2 | 12/2007 | Flaherty et al. |
| 7,399,277 | B2 | 7/2008 | Saidara et al. |
| 7,442,186 | B2 | 10/2008 | Blomquist |
| 7,602,310 | B2 | 10/2009 | Mann et al. |
| 7,647,237 | B2 | 1/2010 | Malave et al. |
| 7,699,807 | B2 | 4/2010 | Faust et al. |
| 7,727,148 | B2 | 6/2010 | Talbot et al. |
| 7,785,313 | B2 | 8/2010 | Mastrototaro |
| 7,806,886 | B2 | 10/2010 | Kanderian, Jr. et al. |
| 7,819,843 | B2 | 10/2010 | Mann et al. |
| 7,828,764 | B2 | 11/2010 | Moberg et al. |
| 7,879,010 | B2 | 2/2011 | Hunn et al. |
| 7,890,295 | B2 | 2/2011 | Shin et al. |
| 7,892,206 | B2 | 2/2011 | Moberg et al. |
| 7,892,748 | B2 | 2/2011 | Norrild et al. |
| 7,901,394 | B2 | 3/2011 | Ireland et al. |
| 7,942,844 | B2 | 5/2011 | Moberg et al. |
| 7,946,985 | B2 | 5/2011 | Mastrototaro et al. |
| 7,955,305 | B2 | 6/2011 | Moberg et al. |
| 7,963,954 | B2 | 6/2011 | Kavazov |
| 7,977,112 | B2 | 7/2011 | Burke et al. |
| 7,979,259 | B2 | 7/2011 | Brown |
| 7,985,330 | B2 | 7/2011 | Wang et al. |
| 8,024,201 | B2 | 9/2011 | Brown |
| 8,100,852 | B2 | 1/2012 | Moberg et al. |
| 8,114,268 | B2 | 2/2012 | Wang et al. |
| 8,114,269 | B2 | 2/2012 | Cooper et al. |
| 8,137,314 | B2 | 3/2012 | Mounce et al. |
| 8,181,849 | B2 | 5/2012 | Bazargan et al. |
| 8,182,462 | B2 | 5/2012 | Istoc et al. |
| 8,192,395 | B2 | 6/2012 | Estes et al. |
| 8,195,265 | B2 | 6/2012 | Goode, Jr. et al. |
| 8,202,250 | B2 | 6/2012 | Stutz, Jr. |
| 8,207,859 | B2 | 6/2012 | Enegren et al. |
| 8,226,615 | B2 | 7/2012 | Bikovsky |
| 8,257,259 | B2 | 9/2012 | Brauker et al. |
| 8,267,921 | B2 | 9/2012 | Yodfat et al. |
| 8,275,437 | B2 | 9/2012 | Brauker et al. |
| 8,277,415 | B2 | 10/2012 | Mounce et al. |
| 8,292,849 | B2 | 10/2012 | Bobroff et al. |
| 8,298,172 | B2 | 10/2012 | Nielsen et al. |
| 8,303,572 | B2 | 11/2012 | Adair et al. |
| 8,305,580 | B2 | 11/2012 | Aasmul |
| 8,308,679 | B2 | 11/2012 | Hanson et al. |
| 8,313,433 | B2 | 11/2012 | Cohen et al. |
| 8,318,443 | B2 | 11/2012 | Norrild et al. |
| 8,323,250 | B2 | 12/2012 | Chong et al. |
| 8,343,092 | B2 | 1/2013 | Rush et al. |
| 8,352,011 | B2 | 1/2013 | Van Antwerp et al. |
| 8,353,829 | B2 | 1/2013 | Say et al. |
| 8,625,796 | B1 * | 1/2014 | Ben Ayed ........... H04W 12/068 380/258 |
| 2007/0123819 | A1 | 5/2007 | Mernoe et al. |
| 2010/0160861 | A1 | 6/2010 | Causey, III et al. |
| 2011/0264035 | A1 * | 10/2011 | Yodfat ................... G16H 80/00 604/66 |
| 2011/0314153 | A1 * | 12/2011 | Bathiche ................. H04L 67/16 709/225 |
| 2013/0183936 | A1 * | 7/2013 | Smtih ................... H04W 12/06 455/411 |

* cited by examiner

FINGERPRINT ENHANCED AUTHENTICATION FOR MEDICAL DEVICES IN WIRELESS NETWORKS

CROSS REFERENCE TO RELATED APPLICATIONS

The present application is a continuation of and claims priority to U.S. patent application Ser. No. 15/686,553 filed on Aug. 25, 2017, which is a divisional patent application claiming the benefit of and priority to U.S. patent application Ser. No. 14/132,347 filed on Dec. 18, 2013 (now issued as U.S. Pat. No. 9,779,226), the contents of which are hereby incorporated by reference in their entirety.

FIELD OF THE INVENTION

This invention relates to portable medical devices, in particular embodiments, methods and systems to enable secure wireless communications between infusion system components such as portable infusion pumps and the controllers thereof.

BACKGROUND OF THE INVENTION

Over the years, bodily characteristics have been determined by obtaining a sample of bodily fluid. For example, diabetics often test for blood glucose levels. Traditional blood glucose determinations have utilized a painful finger prick using a lancet to withdraw a small blood sample. This results in discomfort from the lancet as it contacts nerves in the subcutaneous tissue. The pain of lancing and the cumulative discomfort from multiple needle pricks is a strong reason why patients fail to comply with a medical testing regimen used to determine a change in characteristic over a period of time. Although non-invasive systems have been proposed, or are in development, none to date have been commercialized that are effective and provide accurate results. In addition, all of these systems are designed to provide data at discrete points and do not provide continuous data to show the variations in the characteristic between testing times.

A variety of implantable electrochemical sensors have been developed for detecting and/or quantifying specific agents or compositions in a patient's blood. For instance, glucose sensors have been developed for use in obtaining an indication of blood glucose levels in a diabetic patient. Such readings are useful in monitoring and/or adjusting a treatment regimen which typically includes the regular administration of insulin to the patient. Thus, blood glucose readings improve medical therapies with semi-automated medication infusion pumps of the external type, as generally described in U.S. Pat. Nos. 4,562,751; 4,678,408; and 4,685,903; or automated implantable medication infusion pumps, as generally described in U.S. Pat. No. 4,573,994, which are herein incorporated by reference. Typical thin film sensors are described in commonly assigned U.S. Pat. Nos. 5,390,671; 5,391,250; 5,482,473; and 5,586,553 which are incorporated by reference herein, also see U.S. Pat. No. 5,299,571. Additionally, the wireless controllers or monitors for these continuous sensors provide alarms, updates, trend information and often use sophisticated combination of software and hardware to allow the user to program the controller and/or infusion pump, calibrate the sensor, enter data and view data in the monitor and to provide real-time feedback to the user.

Additionally, the wireless communication between the infusion pump and the controller can make the system susceptible to eavesdropping of confidential patient data and potentially hacking attacks to introduce or execute malicious code or commands. Being able to actively identify, isolate and interrogate unverified, or suspect signals received by the system can greatly enhance patient safety and security.

SUMMARY OF THE DISCLOSURE

An infusion system to administer fluid is disclosed. The infusion system includes an infusion pump having a pump processor, a pump memory and a pump radio to enable bi-directional communication. The pump memory stores a plurality of fingerprint tokens and security conditions. The infusion system further includes a controller with a processor, a controller memory and a controller radio to transmit and receive communication from the pump radio. The controller further includes a fingerprint scanner and a graphical user interface shown on a display, and controls to manipulate the graphical user interface. The graphic user interface and fingerprint scanner enable the controller to scan and determine tokens associated with any scanned fingerprints. Additionally, the bi-directional communication between the infusion pump and the controller establish relative proximity between the infusion pump and the controller such that when the relative proximity exceeds a threshold distance at least one of the plurality of security conditions is automatically matched.

A method to secure wireless transmissions between an infusion device and a controller is also disclosed. The method includes operations that scan a fingerprint and calculate a token based on the scanned fingerprint. The method further includes operations that store the token in memory of the infusion device and monitor a relative distance between the infusion device and the controller. An operation sets a timeout if the relative distance exceeds a distance threshold. The method includes operations that initiate a first security condition if the relative distance exceeds the distance threshold for the timeout while continuing to monitor the relative distance between the infusion device and the controller. The method ends with when an operation requests the token when the relative distance between the infusion device and the controller is within the distance threshold.

In another embodiment another infusion system to administer fluid is disclosed. The infusion system to administer fluid includes an infusion pump having a pump processor, a pump memory and a pump radio to enable bi-directional communication. Further, the pump radio includes a configurable attenuator and the pump memory stores a plurality of security modes. Each of the plurality of security modes configuring the attenuator to receive signals of a predetermined strength. The infusion system further includes a controller having a controller processor, a controller memory, a controller radio to transmit and receive communication from the pump radio. The controller further includes a graphical user interface shown on a display, and controls to manipulate the graphical user interface. The controller being paired with the infusion pump via fingerprint authentication, wherein a security check is performed when the infusion pump receives a suspect signal, the suspect signal not matching the predetermined strength associated with a selected security mode.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

DETAILED DESCRIPTION

Figure 1:
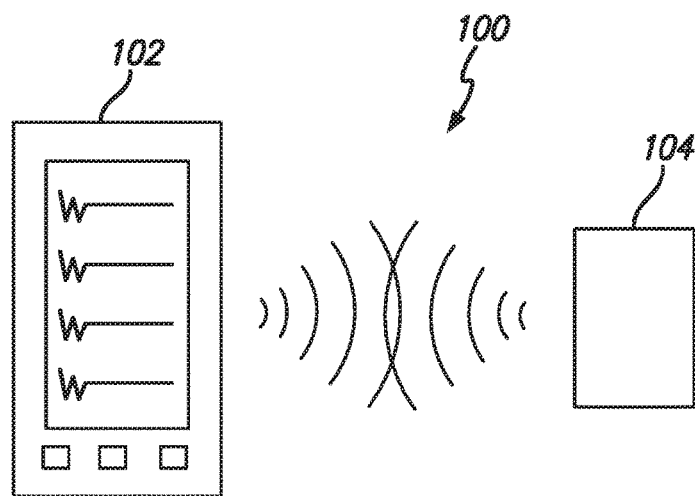
FIG. 1 is an exemplary illustration of components of an infusion system that includes a controller and an infusion pump, in accordance with embodiments of the present invention.

As shown in the drawings for purposes of illustration, the invention is embodied in an infusion system. The infusion system may include an infusion pump, a controller and a sensor assembly. The controller can be used to receive and transmit data from the infusion pump and the sensor. Wireless data transmission can also be used to determine a relative distance separating the controller and the infusion pump. The ability to determine or estimate the relative distance separating the controller and infusion pump can enable various types of enhanced security to protect both data exchanged between the controller and infusion pump and sensitive patient data stored on the infusion pump. In some embodiments similar estimates or determinations of relative distance can be made between the sensor assembly and the controller, or the sensor and the infusion pump. Sensor data can be recorded and stored in a memory associated with the controller. In embodiments of the present invention, the analyte sensor set and monitor system are for determining glucose levels in the blood and/or bodily fluids of the user without the use of, or necessity of, complicated monitoring systems that require user training and interaction. However, it will be recognized that further embodiments of the invention may be used to determine the levels of other analytes or agents, characteristics or compositions, such as hormones, cholesterol, medications concentrations, viral loads (e.g., HIV), or the like. In other embodiments, the monitor system may also include the capability to be programmed to record data at specified time intervals. The monitor system and analyte sensor are primarily adapted for use in subcutaneous human tissue. However, still further embodiments may be placed in other types of tissue, such as muscle, lymph, organ tissue, veins, arteries or the like, and used in animal tissue. The analyte sensors may be subcutaneous sensors, transcutaneous sensors, percutaneous sensors, sub-dermal sensors, skin surface sensors, or the like. Embodiments may record sensor readings on an intermittent or continuous basis.

In embodiments that include real-time determination of body characteristic data various types of analysis can be performed by the infusion pump, the controller or both on the real-time data. The infusion device and controller, being regulated by the Food and Drug Administration, includes various safeguards regarding device security, patient data security, traceability and reporting requirements (e.g., adverse events). Establishing trusted secure data transfer between the controller and the infusion pump in conjunction with various encryption techniques can provide enhanced data security of sensitive patient data stored. The combination of trusted secure data transfer with encryption techniques can help minimize unauthorized malicious insulin delivery commands and/or wireless access to sensitive patient data stored on both the infusion pump and the controller. The use of the techniques described below can further help identify and minimize the likelihood of success of wireless hacking attacks via suspect signals on the system.

FIG. 1 is an exemplary illustration of components of an infusion system 100 that includes a controller 102 and an infusion pump 104, in accordance with embodiments of the present invention. In one embodiment the infusion pump 104 has minimal controls and the controller 102 is the primary interface device to program and verify setting of the infusion pump 104. In one embodiment the controller 104 exchanges data with the infusion pump 104 via bi-directional wireless communications facilitated by radios, optical interconnections such as infra-red or the like.

In embodiments where the infusion pump 104 and the controller 102 communicate wirelessly, the controller 102 can be used to configure or program an associated infusion pump 104 to deliver a basal rate. Additionally, in some other embodiments the controller 102 can be used to program the infusion pump 104 to periodically remind a user via an alert to deliver a bolus. For a basal, once the infusion pump 104 is programmed using the controller 102, the infusion pump 104 can execute the program without further interaction from the controller 102.

For example, using the controller 102 an infusion pump 104 is programmed to deliver a basal rate. Once programmed, the infusion pump 104 will deliver the basal rate without further input from the controller 102 until either a fluid reservoir within the infusion pump is exhausted via the basal rate, the power supply to the infusion pump is exhausted, or another type of delivery failure. Thus, after the infusion pump 104 is programmed, the infusion pump 104 will execute the program independent of the controller 102. The controller 102 can be used to modify or augment the program of an infusion pump 104, however, the infusion pump 104 does not require continual or periodic updates from the controller 102 to execute a stored program.

Figure 2A:
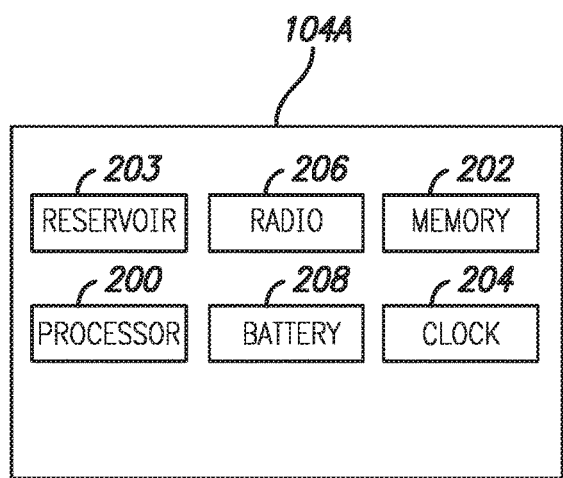
FIGS. 2A and 2B are exemplary block diagrams illustrating select components of two types of infusion pumps, in accordance with embodiments of the present invention.
Figure 2B:
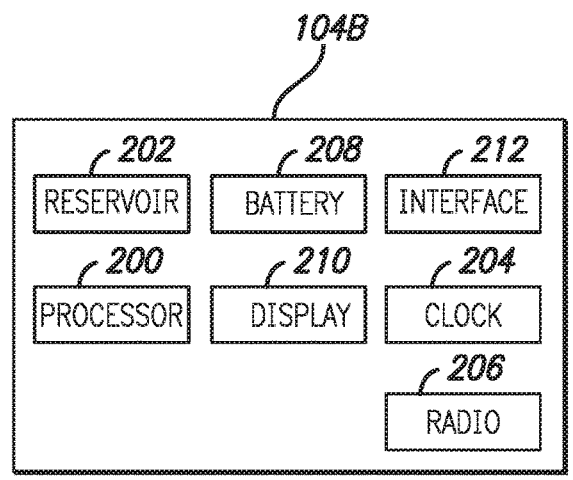

FIGS. 2A and 2B are exemplary block diagrams illustrating select components of two types of infusion pumps 104A and 104B, in accordance with embodiments of the present invention. In one embodiment the infusion pump 104A illustrated in FIG. 2A is a patch pump that is designed to be affixed directly to a user's skin while infusion pump 104B is an external infusion pump such as the Medtronic Minimed Paradigm Revel. As illustrated, the infusion pump 104B includes both a display 210 and an interface 212 that are not found on the infusion pump 104A. In some embodiments the display 210 and the interface 212 found on infusion pump 104B may duplicate some of the control functionality provided by the controller 102 (FIG. 1). While infusion pump 104A does not explicitly have an interface 212, the embodiment illustrated should not be construed to preclude an interface. Infusion pump 104A and similar patch pumps may include interface features such as, but not limited to, buttons, lights, and the like. Both infusion pumps 104A and 104B include a reservoir 203 that contains a fluid that is infused into a user. Additionally, the infusion pumps 104A and 104B also have a processor 200, a memory 202, a clock 204, a radio 206, and a battery 208.

In one embodiment the memory 202 is used to store program instructions that are executed by the processor 200. The memory 202 may also be used to store settings for the infusion pump 104 such as, but not limited to, basal rates for various times of day, and alert and reminder settings/triggers/thresholds along with a plurality of security conditions. In embodiments where the infusion pump 104 is used to deliver insulin, the memory 202 can be used to store information specific to a user such as, but not limited to a carbohydrate-to-insulin ratio (CIR) and an insulin sensitivity factor (ISF) of a user. In all embodiments, the memory 202 may be used in conjunction with the clock 204 to store various alarms, alerts and/or reminders. Some of the various alarms that are associated with the clock 204 are periodic notifications of an infusion or periodic notifications that the user should perform a check of their blood glucose value. Furthermore, the memory 202 can be used to store threshold values to trigger various alarms to notify a user of issues discovered during a diagnostic test of the infusion pump. For example, the memory 202 can include threshold values to determine if there is occlusion of the infusion site, an infusion line, or if a battery needs to be replaced. The types of threshold alarms discussed above are merely exemplary and should not be construed as limiting.

The alarms or alerts are conveyed to a user either audibly or tactilely. Audible alarms can include, but are not limited to audible beeps, chirps, and polyphonic ringtones. Furthermore, a user can adjust the volume of the audible alarms using a simple rocker switch associated with either the controller 102, the infusion pump 104 or in some embodiments, both the controller 102 and the infusion pump 104. In other embodiments another type of user interface, such as a slider displayed via a graphic user interface, a click-wheel type device, or a knob, on the controller 102, the infusion pump 104 or both, can be used to adjust the volume of the alarms. Tactile alarms can be conveyed to the user via vibration from the controller 102, the infusion pump 14 or both. In some embodiments the intensity of the tactile alarms can be adjusted so the tactile alarms are relatively discrete.

Figure 3A:
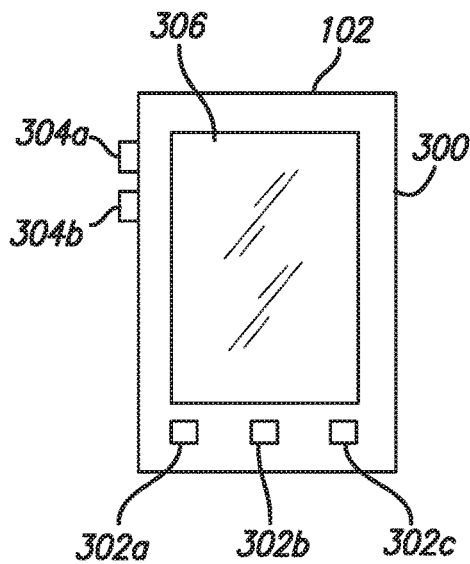
FIG. 3A is an exemplary depiction of controller, in accordance with an embodiment of the present invention.

FIG. 3A is an exemplary depiction of controller 102, in accordance with an embodiment of the present invention. The controller 102 is contained within a case 300 and is generally proportioned to be held in a single hand. The controller 102 includes a screen 306 that in some embodiments is touch sensitive and can be used as the primary interface for a user interface displayed on the screen 306. The orientation of the screen 306 in a portrait mode, as shown in FIG. 3A, should not be perceived as limiting as other embodiments of the controller 102 can have the screen 306 oriented in a landscape mode. Alternatively, the controller 102 can include accelerometers that allow images displayed on the screen 306 to transition between portrait and landscape depending on how a user holds the controller 102. Buttons 302a, 302b, and 302c can further be included in some embodiments of the controller 102.

The buttons 302a, 302b and 302c can be used to provide quick access to different elements of the user interface displayed on the screen 306. Exemplary functions that can be assigned to the buttons 302a, 302b and 302c are navigating the user interface to a previous screen, navigating the user interface to a home page, or bringing up a help screen that defines elements currently displayed on the screen 306. In other embodiments, buttons 302a, 302b and 302c can be replaced with multifunction input capacitive buttons and/or fingerprint readers. While buttons 302a, 302b and 302c are shown, other embodiments of the controller 102 can have fewer buttons, more buttons or even no buttons. In still other embodiments, simultaneously pressing a combination of buttons 302a, 302b and 302c can be associated with particular actions such as automatically muting alarms, powering the controller 102 on or off, rebooting the controller 102, or having the controller 102 enter a diagnostic mode. The particular examples provided are not intended to be limiting and should not be construed to be associated with the simultaneous pressing of buttons. In other embodiments specific sequences of button presses can be used to initiate any of the particular actions discussed above. Furthermore, the location of buttons 302a, 302b and 302c should not be construed as limiting as the case 300 can accommodate the buttons in a variety of locations.

Figure 3B:
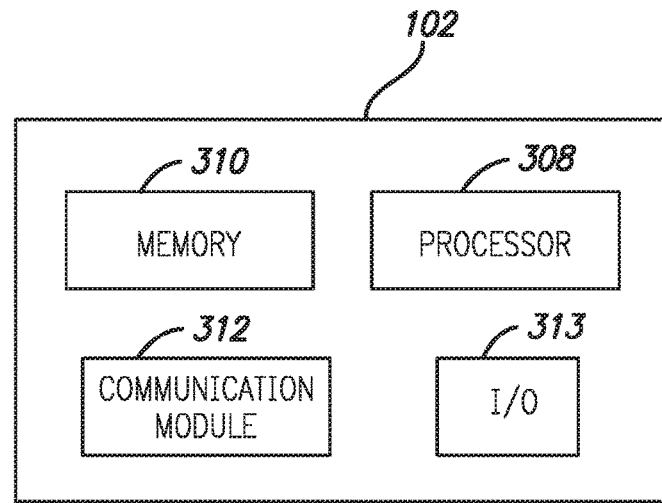
FIG. 3B is an exemplary block diagram showing select elements within the controller, in accordance with one embodiment of the present invention.

FIG. 3B is an exemplary block diagram showing select elements within the controller 102, in accordance with one embodiment of the present invention. The elements discussed below are intended to be exemplary and are not representative of every element within the controller 102. The controller 102 includes a processor 308 that is coupled to a memory 310. In some embodiments the memory 310 is representative of both static RAM and dynamic RAM. Thus, the memory 310 is used to store program instructions that are executed by the processor 308. The program instructions that can be stored in the memory 310 include instructions that render and control a graphical user interface and instructions that allow the controller to communicate with an associated infusion pump (not shown). The memory 310 may also be used to store information specific to a user such as a OR or an ISF. In some embodiments the memory 310 is used to store program information that enables secure pairing between the controller 102 and the infusion pump. The dynamic RAM portion of memory 310 can be used to temporarily hold data such as display data that is to be displayed on the screen. The controller 102 includes I/O controller 313 that can accept input from the variety of buttons or fingerprint readers 302a, 302b, 302c, or buttons 304a and 304b. Input through I/O controller 313 along with execution of program instructions by the processor 308 and memory 310 can allow token generation based on fingerprints to enable secure pairing between the controller and the infusion pump.

The controller 102 further includes a communication module 312. The communications module 312 includes at least one radio that enables wireless communication with the infusion pump. In other embodiments the communication module 312 includes a plurality of radio options that are able to transmit and receive in various communication protocols such as, but not limited to, BlueTooth, Wi-Fi, CDMA, WiMAX, GSM, LTE and the like. In additional embodiments, the communications module 312 is further configured to receive data from a continuous glucose monitoring system. In such embodiments, this allows the controller 102 to receive data from a continuous glucose monitoring system and recommend therapy that can be implemented by the infusion pump.

The graphic user interface displayed on the screen 306 in conjunction with the communication module 312 allows a user to interface and program the infusion pump 104 (FIG. 2). In some embodiments the controller 102 includes multiple profiles that permit different users to exercise different levels of programming control of the infusion pump 104. For example, by entering a password or personal identification number (PIN), a physician could access levels of programming control that are inaccessible to a general user. Similarly, in situations where the infusion pump is worn by a child, the controller 102 can include a parental mode that allows a parent access to programming control that is inaccessible to the child.

Figure 3C:
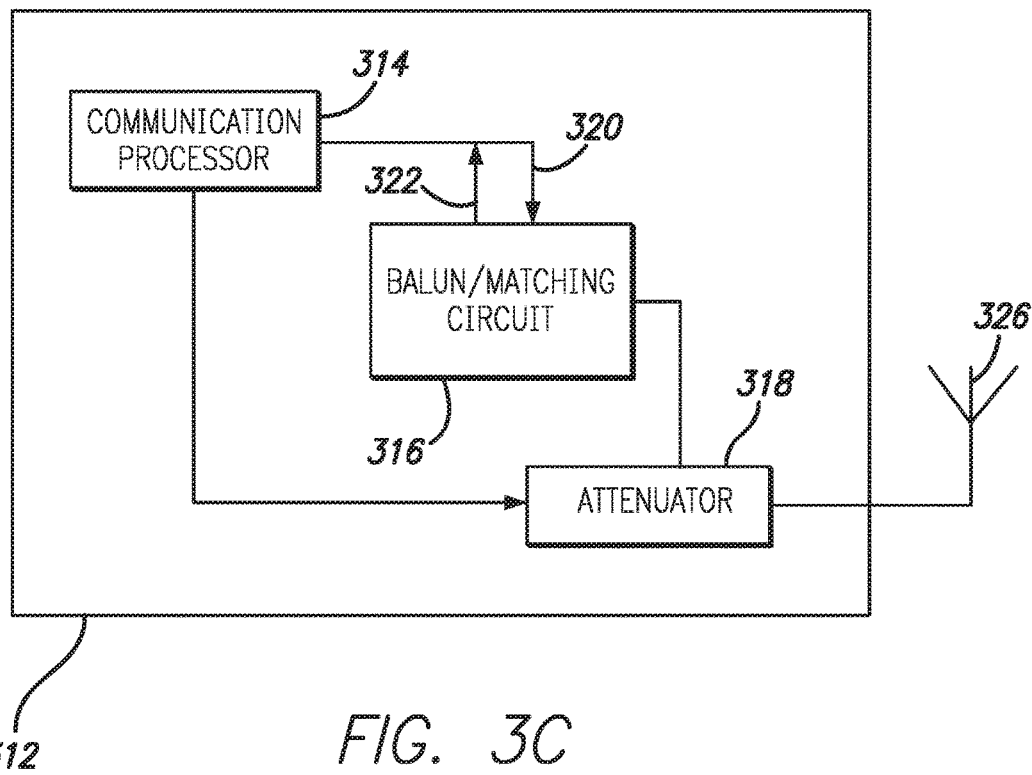
FIG. 3C illustrates exemplary elements within the communication module in accordance with embodiments of the present invention.

FIG. 3C illustrates exemplary elements within the communication module 312 in accordance with embodiments of the present invention. Though FIG. 3C is directed toward the communication module 312 of the controller 102, the radios 206 within infusion pumps 104A and 104B could also be configured to include the exemplary elements discussed below. Thus, in some embodiments the controller 102 and the infusion pump 104 would both include a communication module 312. In still other embodiments only the infusion pump 104 or the controller 102 would contain the communication module 312 while the respective controller 102 or infusion pump 104 would contain radio modules configured to communicate with communication module 312. Communication processor 314 is shown connected to a Balun/matching circuit 316 and a digital attenuator 318. In some embodiments the communication processor 314 is a commercially available BLUETOOTH LOW ENERGY system on chip with RF out 320 going to the Balun/matching circuit 316 which in turn provides feedback RF in 322 along with output to the digital attenuator 318. Digital I/O 324 is further output from the communication processor 314 to the digital attenuator 318. The digital attenuator is shown connected to antenna 326.

By introducing the digital attenuator 318 between the Balun/matching circuit 316 and the antenna, the strength of both the input and output signal from an device having communication module 312 can be altered to implement a type of active security. For example, this active security can allow a user to customize the ability of the infusion pump to transmit and receive signals thereby decreasing or minimizing the likelihood of being a victim of a wireless hacking attack. In a secure environment, no attenuation would be necessary thereby allowing the infusion pump to wireless communicate with elements up to 100 feet away. Whereas in an unsecure environment, the user can utilize the active security resulting in signals from the infusion pump being attenuated so the signal only propagates as few as, or up to six feet, thus making it more difficult for a hacker to interfere with communications between the controller and the infusion pump.

The security level for the communication module 312 is user selectable. In some embodiments the user is allowed to choose between high security, medium security and low security, depending on the type of environment they find themselves. In one embodiment the high security setting restricts receiving and transmission of signals from the infusion pump to less than six feet. In still another embodiment the medium security settings allows receiving and transmitting of signals up to 50 feet. In still other embodiments, the low security setting deactivates the attenuator thereby allowing receipt and transmission of signals to be unfettered from their predetermined settings. In still other embodiments, the low security setting restricts receiving and transmission of signals from the element that includes communication module 312 to 100 feet. The specific examples discussed above regarding the security settings are exemplary and should not be construed as comprehensive or restrictive. It should be generally understood that high security provides the maximum restriction while low security provides the lowest restriction of receipt and transmission of signals from devices having the communication module 312. Similarly, it should be understood that medium security falls between high security and low security. The infusion pump and the controller would exchange the selected security mode during a pairing process that initiates communication and use relative signal strength to determine if spurious or suspect signals are a threat. Once the security level is set, incoming signal strengths to the infusion pump are expected to be within a specified range. If the incoming signal strength is higher than expected based on the selected security mode (e.g. significant strength signal when only a small strength signal is expected) program instructions would identify the suspect signal and execute security check protocols to determine if the suspect signal is blocked or allowed.

Figure 4A:
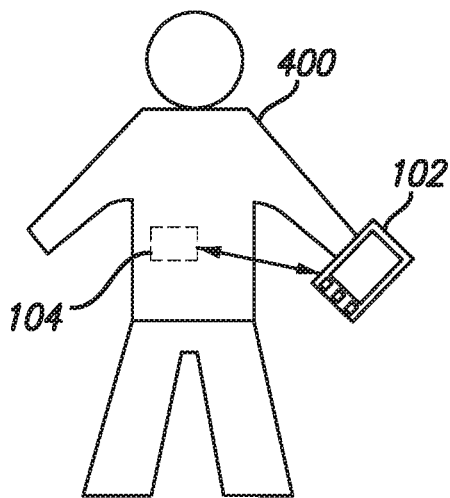
FIGS. 4A and 4B illustrate an exemplary use of the controller with the infusion pump on a user, in accordance with one embodiment of the present invention.
Figure 4B:
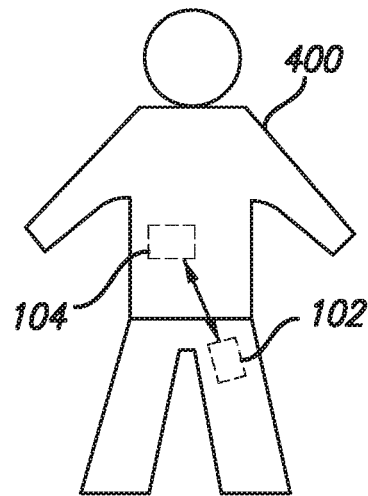

FIGS. 4A and 4B illustrate an exemplary use of the controller 102 with the infusion pump 104 on a user 400, in accordance with one embodiment of the present invention. In FIG. 4A the user 400 is shown wearing an infusion pump 104 under their clothing while holding the controller 102. In FIG. 4B the controller 102 is in the pants pocket of user 400. In these illustration the controller 102 and the infusion pump 104 are paired with a high security mode. As discussed above, the high security mode means the signal strength will be greatly attenuated and each device will anticipate receiving relatively low signal strength signals from the paired device. FIGS. 4A and 4B further illustrate that relative signal strength between the controller 102 and the infusion pump 104 can be used to estimate the relative proximity, or the distance separating the controller 102 and the infusion pump 104. While there may be extraneous signals or physical barriers than interfere with reception, the relative signal strength between the infusion pump 104 and the controller 102 can be used to roughly estimate the proximity or distance separating the devices based on the signals attenuation along the communicating path. Thus, once the infusion pump 104 and the controller 102 are paired, the distance, or relative proximity, between the two can be periodically monitored. If the proximity between the controller 102 and the infusion pump 104 exceeds a threshold distance for a threshold time period, the devices will be considered disconnected, or unpaired.

Figure 5A:
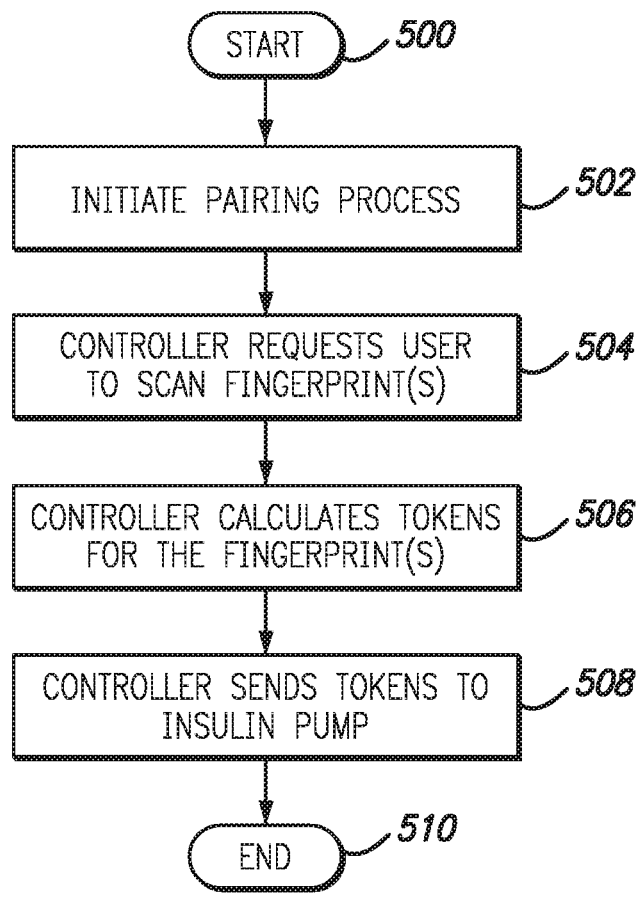
FIG. 5A is an exemplary flow chart illustrating operations to securely pair the controller and the infusion pump, in accordance with embodiments of the present invention.

FIG. 5A is an exemplary flow chart illustrating operations to securely pair the controller and the infusion pump, in accordance with embodiments of the present invention. Operation 500 starts the flow chart while operation 502 initiates the pairing process. In some embodiments, the user interfaces of the controller and the infusion pump allow users to begin pairing the devices via a user's fingerprints.

In embodiments where the controller initiates pairing, operation 504 has the controller requesting the user to scan a fingerprint using the fingerprint scanned discussed regarding FIGS. 3A and 3B. In other embodiments, operation 504 request more than one fingerprint to be scanned. With operation 506 the controller calculates tokens based on the scanned fingerprint or fingerprints. The calculation of tokens reduces data size for both storage and transmission to the infusion pump. Accordingly, operation 508 transmits the fingerprint(s) tokens to the insulin pump to complete the pairing process with END operation 510.

Figure 5B:
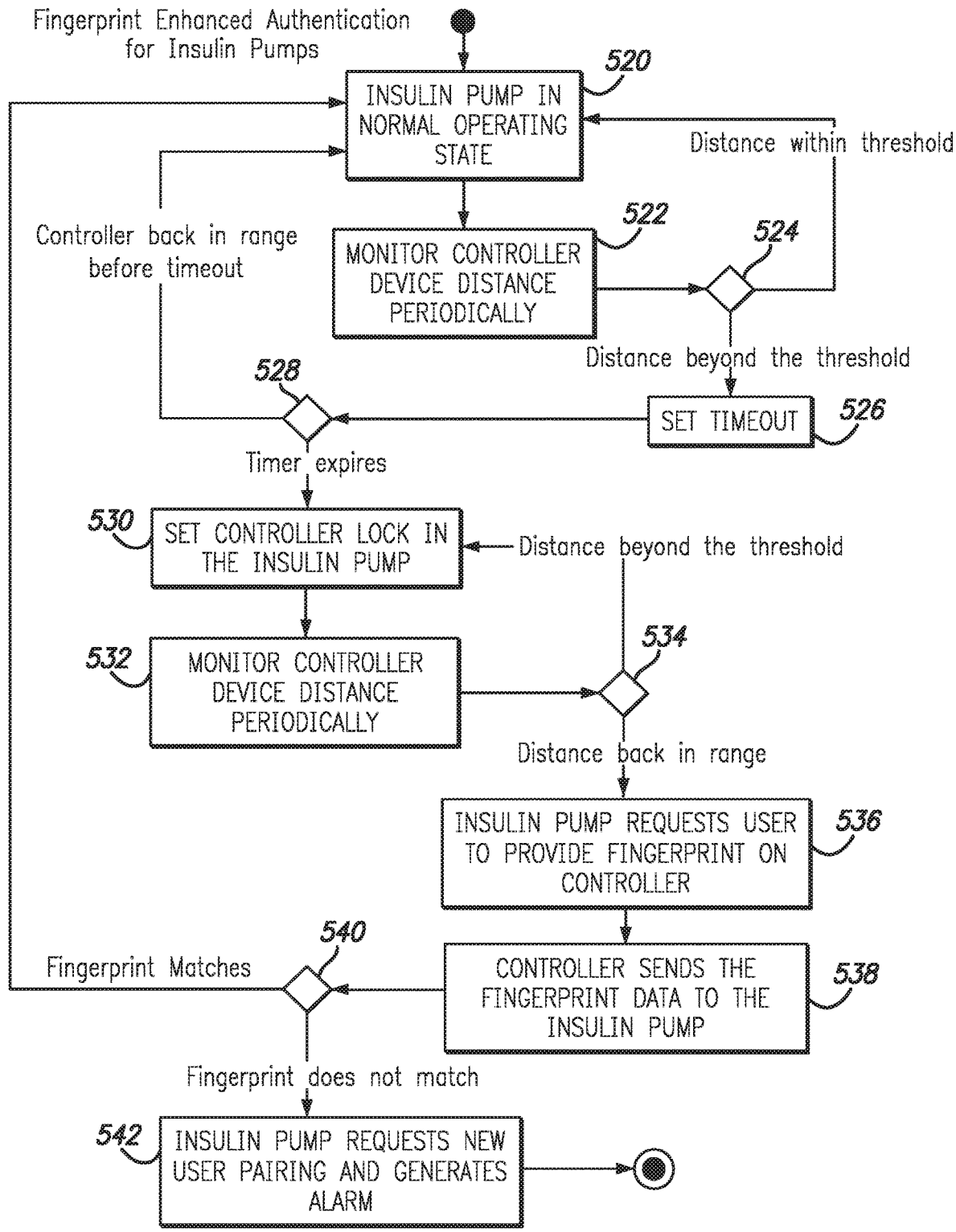
FIG. 5B is an exemplary flow chart illustrating operations where proximity between previously paired devices is estimated based on signal strength and if a threshold distance is exceeded and persists for a preset or threshold period of time the paired devices are disconnected, in accordance with embodiments of the present invention.

FIG. 5B is an exemplary flow chart illustrating operations where proximity between previously paired devices is estimated based on signal strength and if a threshold distance is exceeded and persists for a preset or threshold period of time the paired devices are disconnected, in accordance with embodiments of the present invention. FIG. 5B begins under the assumption that fingerprint enhanced authentication was used to securely pair an infusion pump and controller. Operation 520 has the infusion pump in a normal operating state that flows to operation 522 where the distance between the controller and infusion pump is periodically monitored. In one embodiment the relative signal strength between the controller and infusion pump can be used to estimate a distance between the infusion pump and the controller. Operation 524 queries whether the distance between the devices is beyond or within the threshold distance. If the distance between the two devices is within the threshold, the procedure returns to operation 520. If the distance between the two devices exceeds the threshold, operation 526 sets a timeout.

Operation 528 queries whether the timeout has expired before the controller is determined to be back within the threshold range. If the controller is back in range before the timeout the procedure returns to operation 520. If the timeout expires without the controller coming back into the threshold range operation 530 sets controller lock in the infusion pump. Following operation 530, operation 532 continues to periodically monitor the distance to the controller. Operation 534 queries whether the distance between the controller and the infusion pump is back within the specified threshold distance. If the distance to the controller is beyond the threshold, operation 530 is executed. If the distance between the controller and the infusion pump returns to within the specified threshold range, operation 536 results in the infusion device requesting the user to provide a fingerprint on the controller. Operation 538 follows which has the controller send the fingerprint data to the infusion device. In one embodiment this means sending the token generated from the fingerprint scan to the infusion pump. Operation 540 queries whether the fingerprint sent to the infusion device matches. In some embodiments, this means comparing the received token to the token or tokens received while the devices were initially paired. If the fingerprints match the procedure returns to operation 520. If the fingerprints do not match, operation 542 is executed where a security condition in invoked. In one embodiment the security condition has the infusion device request new user pairing and generates an alarm. In another embodiment, the security condition automatically ceases communication with the controller and generates an alarm to notify the user that the controller has become unpaired. In still another embodiment the security condition may generate an alarm/alert for the user while locking out predetermined command from the controller. In one embodiment the predetermined commands include any command that alters or modifies insulin delivery. Furthermore, in still additional embodiments a preset number of attempts to enter an acceptable fingerprint or token is allowed before the security condition invoked. The various security condition embodiments discussed above are exemplary and should not be considered restrictive or comprehensive. Notification of the user and/or changes to the programming infusion pump in response to a failure to match fingerprints should be considered analogous or within the scope of this disclosure.

While FIGS. 5A and 5B illustrates secure pairing with fingerprints, other embodiments can utilize other methods of out-of-band secure pairing. For additional embodiments see U.S. patent application Ser. No. 14/107,872, filed on Dec. 16, 2013, titled SECURE COMMUNICATIONS BETWEEN ELEMENTS IN A WIRELESS NETWORK, by Kris Holtzclaw which is herein incorporated by reference in its entirety.

Figure 6:
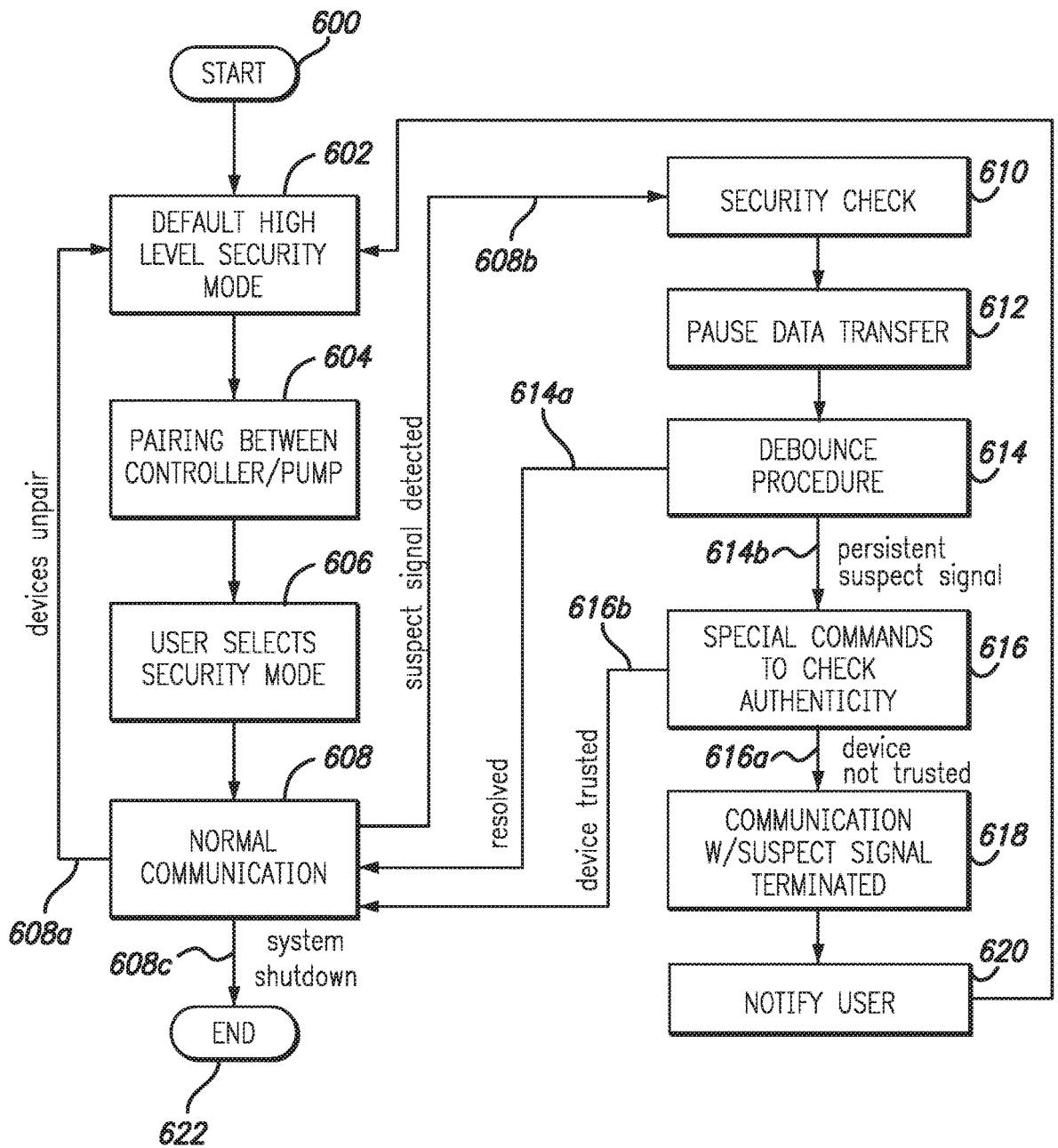
FIG. 6 is an exemplary flowchart illustrating operations to utilize user configurable security modes for securely paired infusion pump and controller, in accordance with embodiments of the present invention.

FIG. 6 is an exemplary flowchart illustrating operations to utilize user configurable security modes for securely paired infusion pump and controller, in accordance with embodiments of the present invention. The flowchart begins with START operation 600 and operation 602 results in high-level security mode or condition being the default security mode between the infusion pump and the controllers. Operation 604 begins the pairing process between the controller and infusion pump (for additional information see FIG. 5). After successfully pairing the infusion pump and controller operation 606 allows the user to select a security mode after which normal communications are established in operation 608. From normal communication 608 the three different options can be undertaken and they include operation 608a where the devices become unpaired, operation 608b where a suspect signal is detected or operation 608c where the system shuts down and the flow chart terminates with END operation 622.

Operation 608a, the devices becoming unpaired, results in returning to operation 602 where the security mode is set to a high-level. There are many potential causes that may lead to the devices becoming unpaired. For example, there may be radio interference with other devices, environmental factors, lower power, software glitches and the like. Regardless of the cause, in embodiment shown in FIG. 6 if the devices become unpaired after having established normal communication 608, the system defaults to a high-level security mode. The specific embodiment shown in FIG. 6 should not be construed as limiting nor as the only option. Various other embodiments can results in different operations being executed while still falling within the scope of this disclosure.

Operation 608b, the detection of a suspect signal, results in execution of operation 610, a security check. A suspect signal is a signal detected by the system that appears to match some characteristics of an expected signal, but may be coming in at a signal strength that is too high or too low for the set security mode. When the controller and pump are paired and the user selects a security mode both the pump and controller transmit and expect to receive signals having signal strength within a specified range for the desired security mode. For example, in a high security mode the digital attenuator will provide high attenuation so any signal transmitted will be intentionally weak, so as to minimize the area in which the signal can be detected. Similarly, the paired device will anticipate receiving a weak signal because the high security mode is selected. In another example, if a low security more is chosen the digital attenuator will provide minimal signal attenuation thereby allowing the device to transmit to a larger area. Accordingly, the paired device will anticipate receiving a higher strength signal than if the security mode was set to medium or high.

Operation 612 suspends or pauses data transfer between the infusion pump and controller after initiation of the security check 610. Execution of operation 614 results in a debounce procedure being performed on the suspect signal such that a single reading of a suspect signal does not forever eliminate communication with a particular device. From operation 614, option 614a results if the debounce procedure is resolved wherein normal communication 608 is resumed. Option 614b results if the debounce procedure results in a persistent suspect signal resulting in operation 616 where special commands are sent to verify authenticity of the suspect signal. Option 616b results if the suspect signal is deemed authentic resulting in return to operation 608, normal communications. Option 616a results if the suspect signal fails to be verified as authentic leading to operation 618 where communication with the suspect signal is terminated. After operation 618, operation 620 notifies the user of the presence of a suspect signal. From operation 620 operation 602 is executed where the default security mode is set to high-level.

Figure 7:
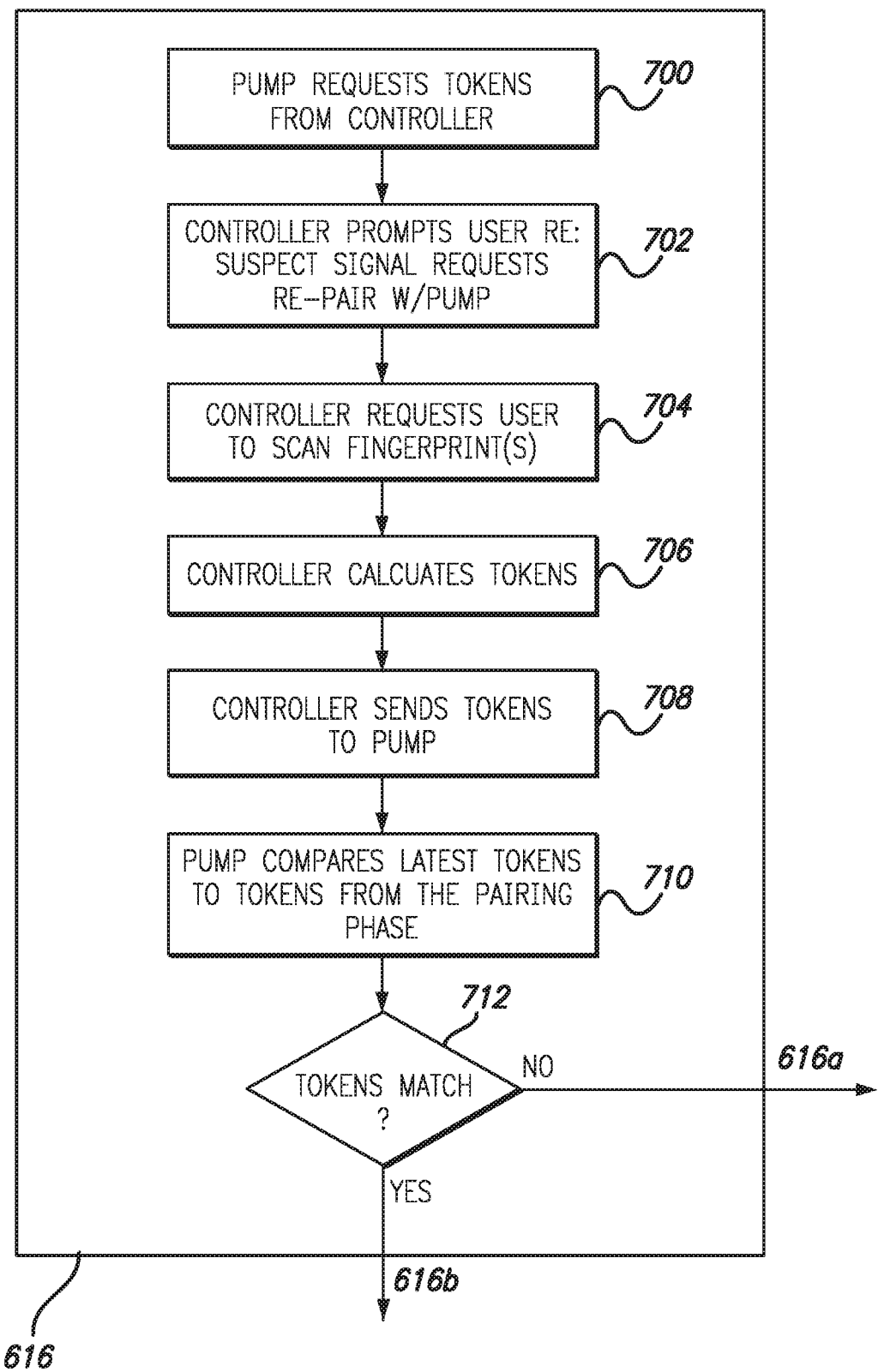
FIG. 7 is an exemplary flow chart illustrating specific operations within operation of FIG. 6, in accordance with embodiments of the present invention.

FIG. 7 is an exemplary flow chart illustrating specific operations within operation 616 of FIG. 6, in accordance with embodiments of the present invention. Operations 700-710 are executed within operation 616 and operation 700 has the pump requesting a pairing token from the controller. Operation 702 results in the controller notifying the user of the suspect signal and requests confirmation of secure communication with the pump. In order to verify secure communication the controller requests the user to scan their fingerprint(s) in operation 704. Operation 706 has the controller recalculate the token from the scanned fingerprints(s) while operation 708 has the controller transmit the tokens to the pump. Operation 710 has the pump compare the token received from the controller to the token from the pairing phase and decision 712 determines if the tokens match. If the tokens match operation 616b is executed while operation 616a is executed if the tokens do not match.

While the description above refers to particular embodiments of the present invention, it will be understood that many modifications may be made without departing from the spirit thereof. The accompanying claims are intended to cover such modifications as would fall within the true scope and spirit of the present invention. The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. An infusion device comprising:
 a radio that enables communication with a controller;
 a memory; and
 a processor coupled to the radio and the memory, the processor programmed to:
   store, in the memory, a token calculated based on a scanned fingerprint;
   monitor a relative distance between the infusion device and the controller;
   set a timeout when the relative distance exceeds a predetermined distance threshold;
   initiate a first security condition when the relative distance exceeds the predetermined distance threshold for the timeout while continuing to monitor the relative distance between the infusion device and the controller; and
   request a token when the relative distance between the infusion device and the controller is within the distance threshold.

2. The infusion device of claim 1, wherein the radio enables communication with a sensor assembly.

3. The infusion device of claim 1, wherein the processor is programmed to alter a strength of an input and an output signal from the infusion device to implement a type of active security.

4. The infusion device of claim 3, wherein processor is programmed to implement the type of active security wherein a user is allowed to customize an ability of the infusion device to transmit and receive signals.

5. The infusion device of claim 4, wherein, in a predetermined secure environment, the ability of the infusion device to transmit and receive signals is not attenuated.

6. The infusion device of claim 3, wherein, in a predetermined unsecure environment, the type of active security comprises attenuating the strength of the input and the output signal.

7. The infusion device of claim 1, wherein the processor is further programmed to: in response to determining that the requested token does not match the stored token, invoking a second security condition comprising requesting new user pairing and generating an alarm.

8. The infusion device of claim 1, wherein the processor is further programmed to: in response to determining that the requested token does not match the stored token, invoking a second security condition comprising automatically ceasing communication with the controller and generating an alarm notifying that the controller has become unpaired.

9. The infusion device of claim 1, wherein the processor is further programmed to: in response to determining that the requested token does not match the stored token, invoking a second security condition comprising generating an alarm or alert while locking out predetermined commands from the controller.

10. The infusion device of claim 1, wherein the processor is further programmed to: after successfully pairing of the infusion device and the controller, receiving user selectable security modes such that both the controller and the infusion device transmit and expect to receive signals within a specified range for user-selected security modes.

11. A method to secure wireless transmissions between an infusion device and a controller, the method comprising:
 storing a token calculated based on a scanned fingerprint;
 monitoring a relative distance between the infusion device and the controller;
 setting a timeout when the relative distance exceeds a distance threshold;
 initiating a first security condition when the relative distance exceeds the distance threshold for the timeout while continuing to monitor the relative distance between the infusion device and the controller; and
 requesting a token when the relative distance between the infusion device and the controller is within the distance threshold.

12. The method to secure wireless transmissions between an infusion device and a controller as described in claim 11, further comprising:
 initiating a second security condition when the token is not received.

13. The method to secure wireless transmissions between an infusion device and a controller as described in claim 11, further comprising:
revoking the first security condition upon receipt of the token.

14. The method to secure wireless transmissions between an infusion device and a controller as described in claim 12, wherein the second security condition locks out commands from the controller that modify insulin delivery.

15. The method to secure wireless transmission between an infusion device and a controller as described in claim 12, wherein the second security condition includes initiating an alarm.

16. One or more non-transitory processor-readable storage media storing instructions which, when executed by one or more processors, cause performance of:
storing a token calculated based on a scanned fingerprint;
monitoring a relative distance between an infusion device and a controller;
setting a timeout when the relative distance exceeds a distance threshold;
initiating a first security condition when the relative distance exceeds the distance threshold for the timeout while continuing to monitor the relative distance between the infusion device and the controller; and
requesting a token when the relative distance between the infusion device and the controller is within the distance threshold.

17. The one or more non-transitory processor-readable storage media of claim 16, wherein initiating the first security condition comprises locking out commands from the controller.

18. The one or more non-transitory processor-readable storage media of claim 16, further storing instructions which, when executed by the one or more processors, cause performance of:
comparing the requested token to the stored token to determine whether the requested token matches the stored token; and
invoking a second security condition when the requested token does not match the stored token.

19. The one or more non-transitory processor-readable storage media of claim 18, wherein invoking the second security condition comprises requesting a new pairing.

20. The one or more non-transitory processor-readable storage media of claim 16, further storing instructions which, when executed by the one or more processors, cause performance of:
prior to storing the token calculated based on the scanned fingerprint, receiving the token calculated based on the scanned fingerprint as part of a pairing process between the infusion device and the controller.

* * * * *